(12) United States Patent
Feather-Henigan

(10) Patent No.: US 8,192,948 B1
(45) Date of Patent: Jun. 5, 2012

(54) CHEMIFLUORESCENT SUBSTRATE FOR PEROXIDE AND PEROXIDASE DETECTION

(75) Inventor: Kelli D. Feather-Henigan, Winnebago, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 417 days.

(21) Appl. No.: 12/425,623

(22) Filed: Apr. 17, 2009

Related U.S. Application Data

(60) Provisional application No. 61/048,313, filed on Apr. 28, 2008.

(51) Int. Cl.
*C12Q 1/28* (2006.01)
(52) U.S. Cl. .......................... 435/28; 435/975
(58) Field of Classification Search ...................... 435/28
See application file for complete search history.

(56) References Cited

U.S. PATENT DOCUMENTS

| 5,171,668 | A  | * | 12/1992 | Sugiyama ........................ 435/28 |
| 6,432,662 | B1 | * | 8/2002  | Davis et al. ...................... 435/28 |
| 2005/0096315 | A1 |  | 5/2005 | Batchelor et al. |

OTHER PUBLICATIONS

Lyon J. et al. Picomolar Peroxide Detection Using a Chemically Activated Redox Mediator and Square Wave Voltammetry. Analytical Chemistry 78(24)8518-25, Dec. 15, 2006.*
Hines K. et al. Luminescence Biotechnology. Chapter 10, pp. 161-177, CRC Press 2002.*

* cited by examiner

*Primary Examiner* — Ralph Gitomer
(74) *Attorney, Agent, or Firm* — Thompson Hine LLP

(57) ABSTRACT

A kit for enhanced detection of analytes that produce peroxide or peroxidase activity.

4 Claims, 5 Drawing Sheets

CHEMIFLUORESCENT SUBSTRATE FOR PEROXIDE AND PEROXIDASE DETECTION

This application claims priority from U.S. Provisional application Ser. No. 61/048,313, filed Apr. 28, 2008.

A composition, method, and kit for detecting and quantitating reactive oxygen species. The composition comprises at least one chemical enhancer that increases a fluorescent signal produced by a resorufin derivative, such as a phenoxazine, upon reaction with, for example, peroxidase in the presence of a peroxide source.

Examples of resorufin derivatives include 10-acetyl-3,7-dihydroxyphenoxazine (ADHP), 2,8-difluoro-10-3,7-dihydroxyphenoxazine, and 10-acetyl-phenoxazine-3,7-diol diacetate. Further examples of resorufin derivatives, including fluorinated resorufin derivatives, are described in U.S. Published Patent Application No. 20050096315, which is incorporated by reference herein in its entirety, and include 2,8-difluoro-3,7-dihydroxyphenoxazine, 2,8-difluoro-3,7,10-triacetylphenoxazine, and 2,8-difluoro-10-acetyl-3,7-dihydroxyphenoxazine. In one embodiment, the composition detects peroxidase activity and/or peroxide, for example, in solution based assays such as enzyme linked immunosorbant assays (ELISA).

Figure 1:
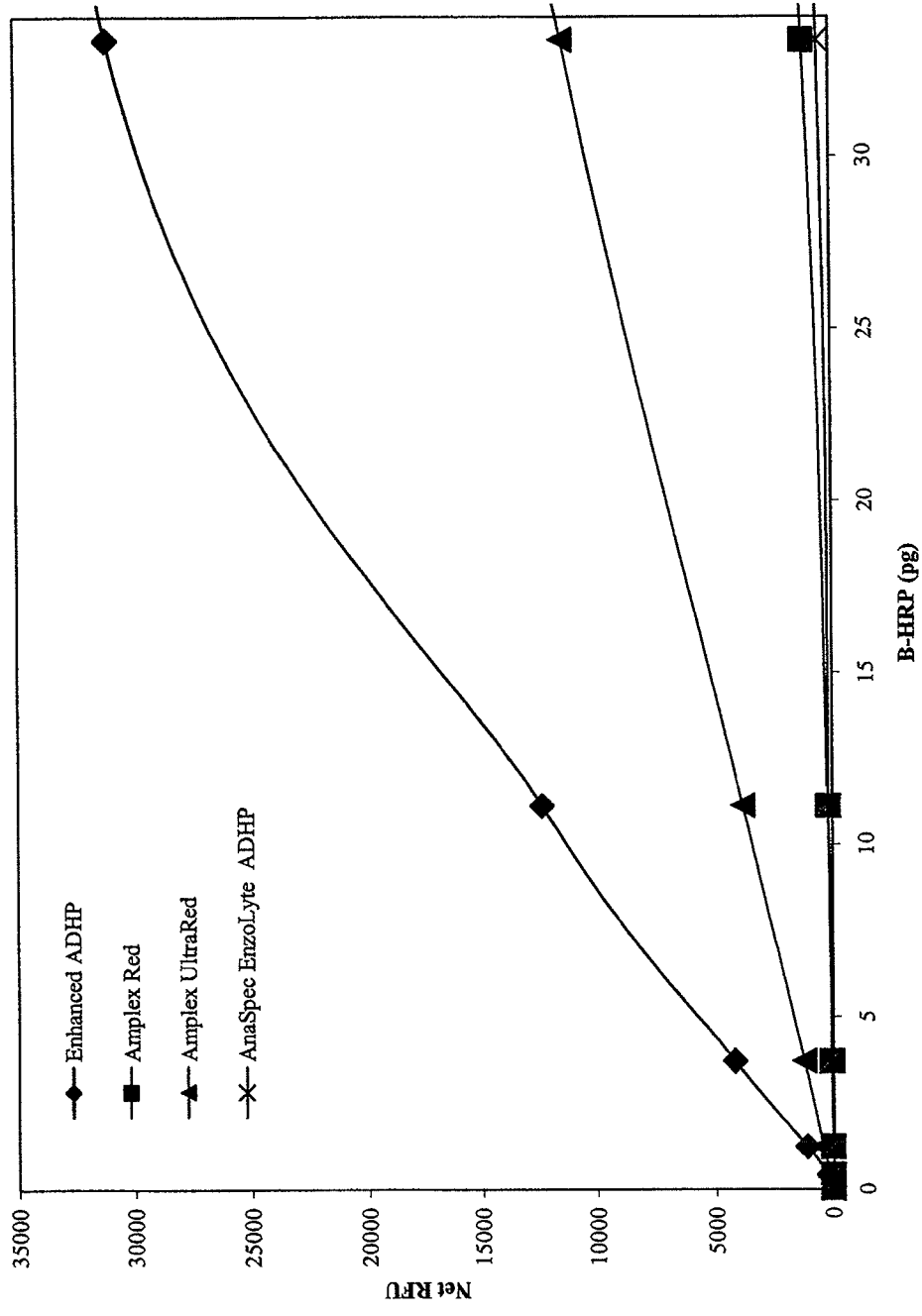
FIG. 1 shows the effect of the 10-acetyl-3,7-dihydroxyphenoxazine (ADHP) substrate versus other substrates in a peroxidase assay.

Resorufin, the structure of which is shown below, is a highly fluorescent compound with excitation and emission maxima of about 570 nm and 585 nm, respectively.

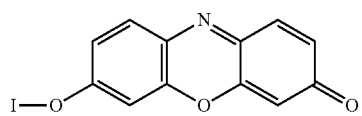

Resorufin

The resorufin derivative 10-acetyl-3,7-dihydroxyphenoxazine (ADHP), the structure of which is shown below

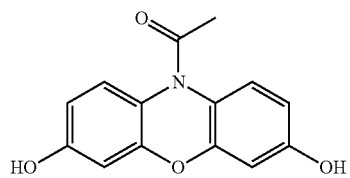

is commonly used as a substrate for detecting and quantitating hydrogen peroxide ($H_2O_2$) or horseradish peroxidase (HRP). Another example of a resorufin derivative is 10-acetyl-phenoxazine-3,7-diol diacetate, the structure of which is shown below

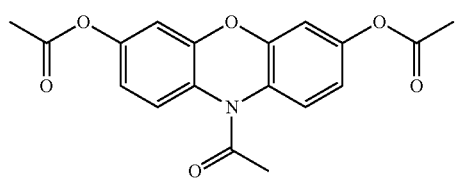

Resorufin derivatives, such as ADHP, react with hydrogen peroxide with a 1:1 stoichiometry to produce resorufin. Resorufin derivatives are used in combination with HRP to detect and quantitate $H_2O_2$ produced during enzyme-coupled reactions, or to detect $H_2O_2$ released from biological samples. As a substrate for peroxidases such as HRP, resorufin derivatives, such as ADHP, are used in combination with a peroxide source to detect and quantitate the amount of peroxidase present in an assay sample.

Resorufin derivatives can be used for detecting a wide variety of analytes that produce peroxide or have peroxide activity. Resorufin derivatives can be used to monitor acetylcholinesterase activity or to detect acetylcholine; measure catalase activity, quantitate cholesterol; monitor galactose oxidase activity or detect galactose; detect glucose and monitor glucose oxidase activity; detect glutamic acid or monitor glutamate oxidase activity; measure monoamine oxidase activity; monitor myeloperoxidase activity; monitor neuraminidase (sialidase) activity; monitor phosphatidylcholine-specific phospholipase C activity; monitor phospholipase D activity, monitor phytase activity; monitor semicarbazide-sensitive amine oxidase activity; monitor sphingomyelinase activity; detect uric acid or monitor uric acid activity; detect xanthine or hypoxanthine; and/or monitor xanthine oxidase activity.

The composition includes a chemical enhancer, such as an azine. Azines can be used alone or in combination as the enhancer. Azines are classified as any of various organic compounds, such as pyridine or pyrimidine, which are a six-membered heterocyclic compounds that contains one or more atoms of nitrogen. In one embodiment, the enhancer is sodium phenothiazine 10-yl propane sulfonate (NaPT). NaPT is described in U.S. Pat. Nos. 6,432,662 and 5,171,668, which are incorporated by reference herein in their entirety.

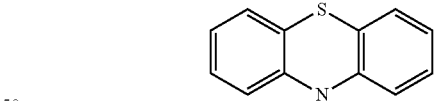

Sodium phenothiazine 10-yl propane sulfonate (NaPT)

In one embodiment, the enhancer is sodium phenothiazine 10-yl propane sulfonate (NaPT). In one embodiment, the enhancer is 10-(3-carboxy-n-propyl) phenothiazine (CPPT). In one embodiment, the enhancer is sodium phenoxazine 10-yl propane sulfonate (NaPX). Azines, including any of those disclosed in U.S. Pat. No. 5,171,668, or any of the water-soluble azines disclosed in U.S. Pat. No. 6,432,662, or combinations of azines, may be used as enhancers. Examples of water soluble azines to be used as enhancers are the 3-(with non-10-H) and 10-alkysulfonates phenothiazine and phenoxazine derivatives. The alkyl groups contain 1-12 carbon atoms that can be the same or different. Water soluble azines can be synthesized by methods known by a person of ordinary skill in the art using commercially available phenoxazine or phenothiazine. In one embodiment, the enhancer is selected from the group consisting of N-methylphenoxazine, N-ethylphenoxazine, N-propylphenoxazine, sodium phenoxazine-10-yl-propanesulfonate, sodium phenoxazine-10-yl-2,4-dimethyl-1,3-butadienesulfonate, 1-methylphenoxazine-10-yl-propylsulfonate, 3-methylphenoxazine-10-yl-propylsulfonate, 6-methylphenoxazine-10-yl-propylsulfonate, 8-methylphenoxazine-10-yl-propylsulfonate, 1,3-dimethylphenoxazine-10-yl-propylsulfonate, 1,6-dimethylphenoxazine-10-yl-propylsulfonate, 1,8-dimethylphenoxazine-10-yl-propylsulfonate, 3,6-dimethylphenoxazine-10-yl-propylsulfonate, 3,8-dimethylphenoxazine-10-yl-propylsulfonate, 6,8-dimethylphenoxazine-10-yl-propylsulfonate, 1,3,6-trimethylphenoxazine-10-yl-propylsulfonate, 1,3,8-trimethylphenoxazine-10-yl-propylsulfonate, 1,6,8-trimethylphenoxazine-10-yl-propylsulfonate, 1-ethylphenoxazine-10-yl-propylsulfonate, 3-ethylphenoxazine-10-yl-propylsulfonate, 6-ethylphenoxazine-10-yl-propylsulfonate, 8-ethylphenoxazine-10-yl-propylsulfonate, 1,3-diethylphenoxazine-10-yl-propylsulfonate, 1,6-diethylphenoxazine-10-yl-propylsulfonate, 1,8-diethylphenoxazine-10-yl-propylsulfonate, 3,6-diethylphenoxazine-10-yl-propylsulfonate, 3,8-diethylphenoxazine-10-yl-propylsulfonate, 6,8-diethylphenoxazine-10-yl-propylsulfonate, 1,3,6-triethylphenoxazine-10-yl-propylsulfonate, 1,3,8-triethylphenoxazine-10-yl-propylsulfonate, 1,6,8-triethylphenoxazine-10-yl-propylsulfonate, 1-propylphenoxazine-10-yl-propylsulfonate, 3-propylphenoxazine-10-yl-propylsulfonate, 6-propylphenoxazine-10-yl-propylsulfonate, 8-propylphenoxazine-10-yl-propylsulfonate, 1,3-dipropylphenoxazine-10-yl-propylsulfonate, 1,6-dipropylphenoxazine-10-yl-propylsulfonate, 1,8-dipropylphenoxazine-10-yl-propylsulfonate, 3,6-dipropylphenoxazine-10-yl-propylsulfonate, 3,8-dipropylphenoxazine-10-yl-propylsulfonate, 6,8-dipropylphenoxazine-10-yl-propylsulfonate, 1,3,6-tripropylphenoxazine-10-yl-propylsulfonate, 1,3,8-tripropylphenoxazine-10-yl-propylsulfonate, 1,6,8-tripropylphenoxazine-10-yl-propylsulfonate, 1-butylphenoxazine-10-yl-propylsulfonate, 3-butylphenoxazine-10-yl-propylsulfonate, 6-butylphenoxazine-10-yl-propylsulfonate, 8-butylphenoxazine-10-yl-propylsulfonate, 1,3-dibutylphenoxazine-10-yl-propylsulfonate, 1,6-dibutylphenoxazine-10-yl-propylsulfonate, 1,8-dibutylphenoxazine-10-yl-propylsulfonate, 3,6-dibutylphenoxazine-10-yl-propylsulfonate, 3,8-dibutylphenoxazine-10-yl-propylsulfonate, 6,8-dibutylphenoxazine-10-yl-propylsulfonate, 1,3,6-tributylphenoxazine-10-yl-propylsulfonate, 1,3,8-tributylphenoxazine-10-yl-propylsulfonate, 1,6,8-tributylphenoxazine-10-yl-propylsulfonate, 1-chlorophenoxazine-10-yl-propylsulfonate, 3-chlorophenoxazine-10-yl-propylsulfonate, 6-chlorophenoxazine-10-yl-propylsulfonate, 8-chlorophenoxazine-10-yl-propylsulfonate, 1-bromophenoxazine-10-yl-propylsulfonate, 3-bromophenoxazine-10-yl-propylsulfonate, 6-bromophenoxazine-10-yl-propylsulfonate, 8-bromophenoxazine-10-yl-propylsulfonate, N-methylphenothiazine, N-ethylphenothiazine, N-propylphenothiazine, sodium phenothiazine-10-yl-propanesulfonate, sodium phenothiazine-10-yl-2,4-dimethyl-1,3-butadienesulfonate, 1-methylphenothiazine-10-yl-propylsulfonate, 3-methylphenothiazine-10-yl-propylsulfonate, 6-methylphenothiazine-10-yl-propylsulfonate, 8-methylphenothiazine-10-yl-propylsulfonate, 1,3-dimethylphenothiazine-10-yl-propylsulfonate, 1,6-dimethylphenothiazine-10-yl-propylsulfonate, 1,8-dimethylphenothiazine-10-yl-propylsulfonate, 3,6-dimethylphenothiazine-10-yl-propylsulfonate, 3,8-dimethylphenothiazine-10-yl-propylsulfonate, 6,8-dimethylphenothiazine-10-yl-propylsulfonate, 1,3,6-trimethylphenothiazine-10-yl-propylsulfonate, 1,3,8-trimethylphenothiazine-10-yl-propylsulfonate, 1,6,8-trimethylphenothiazine-10-yl-propylsulfonate, 1-ethylphenothiazine-10-yl-propylsulfonate, 3-ethylphenothiazine-10-yl-propylsulfonate, 6-ethylphenothiazine-10-yl-propylsulfonate, 8-ethylphenothiazine-10-yl-propylsulfonate, 1,3-diethylphenothiazine-10-yl-propylsulfonate, 1,6-diethylphenothiazine-10-yl-propylsulfonate, 1,8-diethylphenothiazine-10-yl-propylsulfonate, 3,6-diethylphenothiazine-10-yl-propylsulfonate, 3,8-diethylphenothiazine-10-yl-propylsulfonate, 6,8-diethylphenothiazine-10-yl-propylsulfonate, 1,3,6-triethylphenothiazine-10-yl-propylsulfonate, 1,3,8-triethylphenothiazine-10-yl-propylsulfonate, 1,6,8-triethylphenothiazine-10-yl-propylsulfonate, 1-propylphenothiazine-10-yl-propylsulfonate, 3-propylphenothiazine-10-yl-propylsulfonate, 6-propylphenothiazine-10-yl-propylsulfonate, 8-propylphenothiazine-10-yl-propylsulfonate, 1,3-dipropylphenothiazine-10-yl-propylsulfonate, 1,6-dipropylphenothiazine-10-yl-propylsulfonate, 1,8-dipropylphenothiazine-10-yl-propylsulfonate, 3,6-dipropylphenothiazine-10-yl-propylsulfonate, 3,8-dipropylphenothiazine-10-yl-propylsulfonate, 6,8-dipropylphenothiazine-10-yl-propylsulfonate, 1,3,6-tripropylphenothiazine-10-yl-propylsulfonate, 1,3,8-tripropylphenothiazine-10-yl-propylsulfonate, 1,6,8-tripropylphenothiazine-10-yl-propylsulfonate, 1-butylphenothiazine-10-yl-propylsulfonate, 3-butylphenothiazine-10-yl-propylsulfonate, 6-butylphenothiazine-10-yl-propylsulfonate, 8-butylphenothiazine-10-yl-propylsulfonate, 1,3-dibutylphenothiazine-10-yl-propylsulfonate, 1,6-dibutylphenothiazine-10-yl-propylsulfonate, 1,8-dibutylphenothiazine-10-yl-propylsulfonate, 3,6-dibutylphenothiazine-10-yl-propylsulfonate, 3,8-dibutylphenothiazine-10-yl-propylsulfonate, 6,8-dibutylphenothiazine-10-yl-propylsulfonate, 1,3,6-tributylphenothiazine-10-yl-propylsulfonate, 1,3,8-tributylphenothiazine-10-yl-propylsulfonate, 1,6,8-tributylphenothiazine-10-yl-propylsulfonate, 1-chlorophenothiazine-10-yl-propylsulfonate, 3-chlorophenothiazine-10-yl-propylsulfonate, 6-chlorophenothiazine-10-yl-propylsulfonate, 8-chlorophenothiazine-10-yl-propylsulfonate, 1-bromophenothiazine-10-yl-propylsulfonate, 3-bromophenothiazine-10-yl-propylsulfonate, 6-bromophenothiazine-10-yl-propylsulfonate, and 8-bromophenothiazine-10-yl-propylsulfonate, N-methylpyrimidylphenoxazine, N-ethylpyrimidylphenoxazine, N-propylpyrimidylphenoxazine, sodium pyrimidylphenoxazine-10-yl-propanesulfonate, sodium pyrimidylphenoxazine-10-yl-2,4-dimethyl-1,3-butadienesulfonate, 1-methylpyrimidylphenoxazine-10-yl-propylsulfonate, 3-methylpyrimidylphenoxazine-10-yl-propylsulfonate, 6-methylpyrimidylphenoxazine-10-yl-propylsulfonate, 8-methylpyrimidylphenoxazine-10-yl-propylsulfonate, 1,3-dimethylpyrimidylphenoxazine-10-yl-propylsulfonate, 1,6-dimethylpyrimidylphenoxazine-10-yl-propylsulfonate, 1,8-dimethylpyrimidylphenoxazine-10-yl-propylsulfonate, 3,6- dimethylpyrimidylphenoxazine-10-yl-propylsulfonate, 3,8-dimethylpyrimidylphenoxazine-10-yl-propylsulfonate, 6,8-dimethylpyrimidylphenoxazine-10-yl-propylsulfonate, 1,3,6-trimethylpyrimidylphenoxazine-10-yl-propylsulfonate, 1,3,8-trimethylpyrimidylphenoxazine-10-yl-propylsulfonate, 1,6,8-trimethylpyrimidylphenoxazine-10-yl-propylsulfonate, 1-ethylpyrimidylphenoxazine-10-yl-propylsulfonate, 3-ethylpyrimidylphenoxazine-10-yl-propylsulfonate, 6-ethylpyrimidylphenoxazine-10-yl-propylsulfonate, 8-ethylpyrimidylphenoxazine-10-yl-propylsulfonate, 1,3-diethylpyrimidylphenoxazine-10-yl-propylsulfonate, 1,6-diethylpyrimidylphenoxazine-10-yl-propylsulfonate, 1,8-diethylpyrimidylphenoxazine-10-yl-propylsulfonate, 3,6-diethylpyrimidylphenoxazine-10-yl-propylsulfonate, 3,8-diethylpyrimidylphenoxazine-10-yl-propylsulfonate, 6,8-diethylpyrimidylphenoxazine-10-yl-propylsulfonate, 1,3,6-triethylpyrimidylphenoxazine-10-yl-propylsulfonate, 1,3,8-triethylpyrimidylphenoxazine-10-yl-propylsulfonate, 1,6,8-triethylpyrimidylphenoxazine-10-yl-propylsulfonate, 1-propylpyrimidylphenoxazine-10-yl-propylsulfonate, 3-propylpyrimidylphenoxazine-10-yl-propylsulfonate, 6-propylpyrimidylphenoxazine-10-yl-propylsulfonate, 8-propylpyrimidylphenoxazine-10-yl-propylsulfonate, 1,3-dipropylpyrimidylphenoxazine-10-yl-propylsulfonate, 1,6-dipropylpyrimidylphenoxazine-10-yl-propylsulfonate, 1,8-dipropylpyrimidylphenoxazine-10-yl-propylsulfonate, 3,6-dipropylpyrimidylphenoxazine-10-yl-propylsulfonate, 3,8-dipropylpyrimidylphenoxazine-10-yl-propylsulfonate, 6,8-dipropylpyrimidylphenoxazine-10-yl-propylsulfonate, 1,3,6-tripropylpyrimidylphenoxazine-10-yl-propylsulfonate, 1,3,8-tripropylpyrimidylphenoxazine-10-yl-propylsulfonate, 1,6,8-tripropylpyrimidylphenoxazine-10-yl-propylsulfonate, 1-butylpyrimidylphenoxazine-10-yl-propylsulfonate, 3-butylpyrimidylphenoxazine-10-yl-propylsulfonate, 6-butylpyrimidylphenoxazine-10-yl-propylsulfonate, 8-butylpyrimidylphenoxazine-10-yl-propylsulfonate, 1,3-dibutylpyrimidylphenoxazine-10-yl-propylsulfonate, 1,6-dibutylpyrimidylphenoxazine-10-yl-propylsulfonate, 1,8-dibutylpyrimidylphenoxazine-10-yl-propylsulfonate, 3,6-dibutylpyrimidylphenoxazine-10-yl-propylsulfonate, 3,8-dibutylpyrimidylphenoxazine-10-yl-propylsulfonate, 6,8-dibutylpyrimidylphenoxazine-10-yl-propylsulfonate, 1,3,6-tributylpyrimidylphenoxazine-10-yl-propylsulfonate, 1,3,8-tributylpyrimidylphenoxazine-10-yl-propylsulfonate, 1,6,8-tributylpyrimidylphenoxazine-10-yl-propylsulfonate, 1-chloropyrimidylphenoxazine-10-yl-propylsulfonate, 3-chloropyrimidylphenoxazine-10-yl-propylsulfonate, 6-chloropyrimidylphenoxazine-10-yl-propylsulfonate, 8-chloropyrimidylphenoxazine-10-yl-propylsulfonate, 1-bromopyrimidylphenoxazine-10-yl-propylsulfonate, 3-bromopyrimidylphenoxazine-10-yl-propylsulfonate, 6-bromopyrimidylphenoxazine-10-yl-propylsulfonate, 8-bromopyrimidylphenoxazine-10-yl-propylsulfonate, N-methylpyrimidylphenothiazine, N-ethylpyrimidylphenothiazine, N-propylpyrimidylphenothiazine, sodium pyrimidylphenothiazine-10-yl-propanesulfonate, sodium pyrimidylphenothiazine-10-yl-2,4-dimethyl-1,3-butadienesulfonate, 1-methylpyrimidylphenothiazine-10-yl-propylsulfonate, 3-methylpyrimidylphenothiazine-10-yl-propylsulfonate, 6-methylpyrimidylphenothiazine-10-yl-propylsulfonate, 8-methylpyrimidylphenothiazine-10-yl-propylsulfonate, 1,3-dimethylpyrimidylphenothiazine-10-yl-propylsulfonate, 1,6-dimethylpyrimidylphenothiazine-10-yl-propylsulfonate, 1,8-dimethylpyrimidylphenothiazine-10-yl-propylsulfonate, 3,6-dimethylpyrimidylphenothiazine-10-yl-propylsulfonate, 3,8-dimethylpyrimidylphenothiazine-10-yl-propylsulfonate, 6,8-dimethylpyrimidylphenothiazine-10-yl-propylsulfonate, 1,3,6-trimethylpyrimidylphenothiazine-10-yl-propylsulfonate, 1,3,8-trimethylpyrimidylphenothiazine-10-yl-propylsulfonate, 1,6,8-trimethylpyrimidylphenothiazine-10-yl-propylsulfonate, 1-ethylpyrimidylphenothiazine-10-yl-propylsulfonate, 3-ethylpyrimidylphenothiazine-10-yl-propylsulfonate, 6-ethylpyrimidylphenothiazine-10-yl-propylsulfonate, 8-ethylpyrimidylphenothiazine-10-yl-propylsulfonate, 1,3-diethylpyrimidylphenothiazine-10-yl-propylsulfonate, 1,6-diethylpyrimidylphenothiazine-10-yl-propylsulfonate, 1,8-diethylpyrimidylphenothiazine-10-yl-propylsulfonate, 3,6-diethylpyrimidylphenothiazine-10-yl-propylsulfonate, 3,8-diethylpyrimidylphenothiazine-10-yl-propylsulfonate, 6,8-diethylpyrimidylphenothiazine-10-yl-propylsulfonate, 1,3,6-triethylpyrimidylphenothiazine-10-yl-propylsulfonate, 1,3,8-triethylpyrimidylphenothiazine-10-yl-propylsulfonate, 1,6,8-triethylpyrimidylphenothiazine-10-yl-propylsulfonate, 1-propylpyrimidylphenothiazine-10-yl-propylsulfonate, 3-propylpyrimidylphenothiazine-10-yl-propylsulfonate, 6-propylpyrimidylphenothiazine-10-yl-propylsulfonate, 8-propylpyrimidylphenothiazine-10-yl-propylsulfonate, 1,3-dipropylpyrimidylphenothiazine-10-yl-propylsulfonate, 1,6-dipropylpyrimidylphenothiazine-10-yl-propylsulfonate, 1,8-dipropylpyrimidylphenothiazine-10-yl-propylsulfonate, 3,6-dipropylpyrimidylphenothiazine-10-yl-propylsulfonate, 3,8-dipropylpyrimidylphenothiazine-10-yl-propylsulfonate, 6,8-dipropylpyrimidylphenothiazine-10-yl-propylsulfonate, 1,3,6-tripropylpyrimidylphenothiazine-10-yl-propylsulfonate, 1,3,8-tripropylpyrimidylphenothiazine-10-yl-propylsulfonate, 1,6,8-tripropylpyrimidylphenothiazine-10-yl-propylsulfonate, 1-butylpyrimidylphenothiazine-10-yl-propylsulfonate, 3-butylpyrimidylphenothiazine-10-yl-propylsulfonate, 6-butylpyrimidylphenothiazine-10-yl-propylsulfonate, 8-butylpyrimidylphenothiazine-10-yl-propylsulfonate, 1,3-dibutylpyrimidylphenothiazine-10-yl-propylsulfonate, 1,6-dibutylpyrimidylphenothiazine-10-yl-propylsulfonate, 1,8-dibutylpyrimidylphenothiazine-10-yl-propylsulfonate, 3,6-dibutylpyrimidylphenothiazine-10-yl-propylsulfonate, 3,8-dibutylpyrimidylphenothiazine-10-yl-propylsulfonate, 6,8-dibutylpyrimidylphenothiazine-10-yl-propylsulfonate, 1,3,6-tributylpyrimidylphenothiazine-10-yl-propylsulfonate, 1,3,8-tributylpyrimidylphenothiazine-10-yl-propylsulfonate, 1,6,8-tributylpyrimidylphenothiazine-10-yl-propylsulfonate, 1-chloropyrimidylphenothiazine-10-yl-propylsulfonate, 3-chloropyrimdiylphenothiazine-10-yl-propylsulfonate, 6-chloropyrimidylphenothiazine-10-yl-propylsulfonate, 8-chloropyrimidylphenothiazine-10-yl-propylsulfonate, 1-bromopyrimidylphenothiazine-10-yl-propylsulfonate, 3-bromopyrimidylphenothiazine-10-yl-propylsulfonate, 6-bromopyrimidylphenothiazine-10-yl-propylsulfonate, and 8-bromopyrimidylphenothiazine-10-yl-propylsulfonate, N-methylpyridylphenoxazine, N-ethylpyridylphenoxazine, N-propylpyridylphenoxazine, sodium pyridylphenoxazine-10-yl-propanesulfonate, sodium pyridylphenoxazine-10-yl-2,4-dimethyl-1,3-butadienesulfonate, 3-methylpyridylphenoxazine-10-yl-propylsulfonate, 6-methylpyridylphenoxazine-10-yl-propylsulfonate, 8-methylpyridylphenoxazine-10-yl-propylsulfonate, 3,6-dimethylpyridylphenoxazine-10-yl-propylsulfonate, 3,8-dimethylpyridylphenoxazine-10-yl-propylsulfonate, 6,8-dimethylpyridylphenoxazine-10-yl-propylsulfonate, 3-ethylpyridylphenoxazine-10-yl-propylsulfonate, 6-ethylpyridylphenoxazine-10-yl-propylsulfonate, 8-ethylpyridylphenoxazine-10-yl-propylsulfonate, 3,6-diethylpyridylphenoxazine-10-yl-propylsulfonate, 3,8-diethylpyridylphenoxazine-10-yl-propylsulfonate, 6,8-diethylpyridylphenoxazine-10-yl-propylsulfonate, 3-propylpyridylphenoxazine-10-yl-propylsulfonate, 6-propylpyridylphenoxazine-10-yl-propylsulfonate, 8-propylpyridylphenoxazine-10-yl-propylsulfonate, 3,6-dipropylpyridylphenoxazine-10-yl-propylsulfonate, 3,8-dipropylpyridylphenoxazine-10-yl-propylsulfonate, 6,8-dipropylpyridylphenoxazine-10-yl-propylsulfonate, 3-butylpyridylphenoxazine-10-yl-propylsulfonate, 6-butylpyridylphenoxazine-10-yl-propylsulfonate, 8-butylpyridylphenoxazine-10-yl-propylsulfonate, 3,6-dibutylpyridylphenoxazine-10-yl-propylsulfonate, 3,8-dibutylpyridylphenoxazine-10-yl-propylsulfonate, 6,8-dibutylpyridylphenoxazine-10-yl-propylsulfonate, 3-chloropyridylphenoxazine-10-yl-propylsulfonate, 6-chloropyridylphenoxazine-10-yl-propylsulfonate, 8-chloropyridylphenoxazine-10-yl-propylsulfonate, 3-bromopyridylphenoxazine-10-yl-propylsulfonate, 6-bromopyridylphenoxazine-10-yl-propylsulfonate, 8-bromopyridylphenoxazine-10-yl-propylsulfonate, N-methylpyridylphenothiazine, N-ethylpyridylphenothiazine, N-propylpyridylphenothiazine, sodium pyridylphenothiazine-10-yl-propanesulfonate, sodium pyridylphenothiazine-10-yl-2,4-dimethyl-1,3-butadienesulfonate, 3-methylpyridylphenothiazine-10-yl-propylsulfonate, 6-methylpyridylphenothiazine-10-yl-propylsulfonate, 8-methylpyridylphenothiazine-10-yl-propylsulfonate, 3,6-dimethylpyridylphenothiazine-10-yl-propylsulfonate, 3,8-dimethylpyridylphenothiazine-10-yl-propylsulfonate, 6,8-dimethylpyridylphenothiazine-10-yl-propylsulfonate, 3-ethylpyridylphenothiazine-10-yl-propylsulfonate, 6-ethylpyridylphenothiazine-10-yl-propylsulfonate, 8-ethylpyridylphenothiazine-10-yl-propylsulfonate, 3,6-diethylpyridylphenothiazine-10-yl-propylsulfonate, 3,8-diethylpyridylphenothiazine-10-yl-propylsulfonate, 6,8-diethylpyridylphenothiazine-10-yl-propylsulfonate, 3-propylpyridylphenothiazine-10-yl-propylsulfonate, 6-propylpyridylphenothiazine-10-yl-propylsulfonate, 8-propylpyridylphenothiazine-10-yl-propylsulfonate, 3,6-dipropylpyridylphenothiazine-10-yl-propylsulfonate, 3,8-dipropylpyridylphenothiazine-10-yl-propylsulfonate, 6,8-dipropylpyridylphenothiazine-10-yl-propylsulfonate, 3-butylpyridylphenothiazine-10-yl-propylsulfonate, 6-butylpyridylphenothiazine-10-yl-propylsulfonate, 8-butylpyridylphenothiazine-10-yl-propylsulfonate, 3,6-dibutylpyridylphenothiazine-10-yl-propylsulfonate, 3,8-dibutylpyridylphenothiazine-10-yl-propylsulfonate, 6,8-dibutylpyridylphenothiazine-10-yl-propylsulfonate, 3-chloropyridylphenothiazine-10-yl-propylsulfonate, 6-chloropyridylphenothiazine-10-yl-propylsulfonate, 8-chloropyridylphenothiazine-10-yl-propylsulfonate, 3-bromopyridylphenothiazine-10-yl-propylsulfonate, 6-bromopyridylphenothiazine-10-yl-propylsulfonate, and 8-bromopyridylphenothiazine-10-yl-propylsulfonate, N-methyldipyrazinophenoxazine, N-ethyldipyrazinophenoxazine, N-propyldipyrazinophenoxazine, sodium dipyrazinophenoxazine-10-yl-propanesulfonate, sodium dipyrazinophenoxazine-10-yl-2,4-dimethyl-1,3-butadienesulfonate, 3-methyldipyrazinophenoxazine-10-yl-propylsulfonate, 6-methyldipyrazinophenoxazine-10-yl-propylsulfonate, 3,6-dimethyldipyrazinophenoxazine-10-yl-propylsulfonate, 3-ethyldipyrazinophenoxazine-10-yl-propylsulfonate, 6-ethyldipyrazinophenoxazine-10-yl-propylsulfonate, 3,6-diethyldipyrazinophenoxazine-10-yl-propylsulfonate, 3-propyldipyrazinophenoxazine-10-yl-propylsulfonate, 6-propyldipyrazinophenoxazine-10-yl-propylsulfonate, 3,6-dipropyldipyrazinophenoxazine-10-yl-propylsulfonate, 3-butyldipyrazinophenoxazine-10-yl-propylsulfonate, 6-butyldipyrazinophenoxazine-10-yl-propylsulfonate, 3,6-dibutyldipyrazinophenoxazine-10-yl-propylsulfonate, 3-chlorodiyrazinophenoxazine-10-yl-propylsulfonate, 6-chlorodipyrazinophenoxazine-10-yl-propylsulfonate, 3-bromodipyrazinophenoxazine-10-yl-propylsulfonate, 6-bromodipyrazinophenoxazine-10-yl-propylsulfonate, N-methyldipyrazinophenothiazine, N-ethyldipyrazinophenothiazine, N-propyldipyrazinophenothiazine, sodium dipyrazinophenothiazine-10-yl-propanesulfonate, sodium dipyrazinophenothiazine-10-yl-2,4-dimethyl-1,3-butadienesulfonate, 3-methyldipyrazinophenothiazine-10-yl-propylsulfonate, 6-methyldipyrazinophenothiazine-10-yl-propylsulfonate, 3,6-dimethyldipyrazinophenothiazine-10-yl-propylsulfonate, 3-ethyldipyrazinophenothiazine-10-yl-propylsulfonate, 6-ethyldipyrazinophenothiazine-10-yl-propylsulfonate, 3,6-diethyldipyrazinophenothiazine-10-yl-propylsulfonate, 3-propyldipyrazinophenothiazine-10-yl-propylsulfonate, 6-propyldipyrazinophenothiazine-10-yl-propylsulfonate, 3,6-dipropyldipyrazinophenothiazine-10-yl-propylsulfonate, 3-butyldipyrazinophenothiazine-10-yl-propylsulfonate, 6-butyldipyrazinophenothiazine-10-yl-propylsulfonate, 3,6-dibutyldipyrazinophenothiazine-10-yl-propylsulfonate, 3-chlorodipyrazinophenothiazine-10-yl-propylsulfonate, 6-chlorodipyrazinophenothiazine-10-yl-propylsulfonate, 3-bromodipyrazinophenothiazine-10-yl-propylsulfonate, 6-bromodipyrazinophenothiazine-10-yl-propylsulfonate, and combinations thereof.

In one embodiment, the composition comprises an enhancer in combination with at least one of a nucleophilic or organic base catalyst and an imidazole (IM). In one embodiment, the organic base catalyst is dimethylaminopyridine (DMAP). In one embodiment, the imidazole is 2-methylimidazole, 4-methylimidazole.

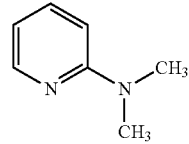

2-(dimethylamino)pyridine (DMAP)

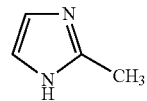

2-methylimidazole (2-MIM)

In one embodiment, the azine is present in the chemifluorescent assay mixture at a concentration from about 0.1 mM to about 10 mM.

An example of nucleophilic or organic base catalyst includes dimethylaminopyridine (DMAP). In one embodiment, the nucleophilic or organic base catalyst is present in the chemifluorescent assay mixture at a concentration from about 1 mM to about 20 mM.

Imidazole (IM) is a heterocyclic aromatic organic compound having the formula $C_3H_4N_2$ and forms a class of compounds known as imidazoles with a similar ring structure as the parent compound but varying substituents. Examples of imidazole compounds include 2-methyl imidazole and 4-methyl imidazole. In one embodiment, the imidazole is present in the chemifluorescent assay mixture at a concentration from about 1 mM to about 20 mM.

In one embodiment, a kit includes an enhancer, a nucleophilic and/or organic base catalyst, and/or an imidazole, a resorufin derivative, a peroxide source, and a buffer solution. In one embodiment, the buffer solution maintains the pH between about pH 6 to about pH 9. Examples of buffers include, but are not limited to, tris(hydroxymethyl)methylamine (tris), phosphate buffered saline (PBS), and borate buffers.

In one embodiment, a method is provided that detects and quantitates reactive oxygen species and their production, for example, peroxide and peroxidase activity. In one embodiment, peroxide and peroxidase activity are detected and quantitated using a resorufin derivative as a substrate. In one embodiment, the method comprises incubating a peroxidase with a resorufin derivative along with a chemical enhancer, and at least one of a nucleophilic and/or organic base catalyst or an imidazole. In one embodiment, the method results in an increased production of the chemifluorescent molecule resorufin.

In one embodiment, the chemifluorescent assay comprises 10-acetyl-3,7-dihydroxyphenoxazine (ADHP) at a concentration from about 10 µM to about 100 µM; sodium phenothiazine 10-yl propane sulfonate (azine, NaPT) at a concentration from about 0.1 mM to about 10 mM; dimethylamino pyridine (DMAP) at a concentration from about 1 mM to about 20 mM; a peroxide source, such as hydrogen peroxide or sodium perborate, at a concentration from about 1 mM to about 20 mM; in an aqueous buffer at a pH from about 6 to about 8, such as tris buffered saline (TBS) or phosphate buffered saline (PBS) and dimethyl sulfoxide (to dissolve the ADHP).

The following examples further illustrate embodiments of the use of the composition and/or kit.

EXAMPLE 1

The composition comprising NaPT and DMAP enhanced the fluorescent product (resorufin) generated by the ADHP reaction with HRP, in the presence of a peroxide source, as shown in FIG. 1.

Various commercially available substrate solutions were prepared according to manufacturers instructions. The enhanced ADHP substrate was prepared by dissolving 6 mM NaPT and 5 mM DMAP in the ADHP (Amplex Red® reagent, Invitrogen) substrate solution. The substrates, NaPT/DMAP enhanced ADHP substrate, Amplex Red® reagent, Amplex UltraRed® reagent (Invitrogen), and SensoLyte® ADHP (AnaSpec) were added to the wells of a black 96 well microplate. A standard curve of biotinylated horseradish peroxidase (B-HRP) was prepared in TBS so that the final concentrations added to the wells of the plate were 100 pg, 33.3 pg, 11.1 pg, 3.07 pg, 1.23 pg, 0.41 pg, and 0.14 pg. The B-HRP dilutions and a TBS blank were added to the wells of the plate and incubated for five minutes. The fluorescence production was measured using a Tecan Safire Fluorometer with excitation at 560 nm and emission at 590 nm.

As shown in FIG. 1, the results show an increase in signal intensity of as much as 90 fold using NaPT/DMAP enhanced ADHP, depending on the HRP concentration and with background subtracted.

EXAMPLE 2

Figure 2:
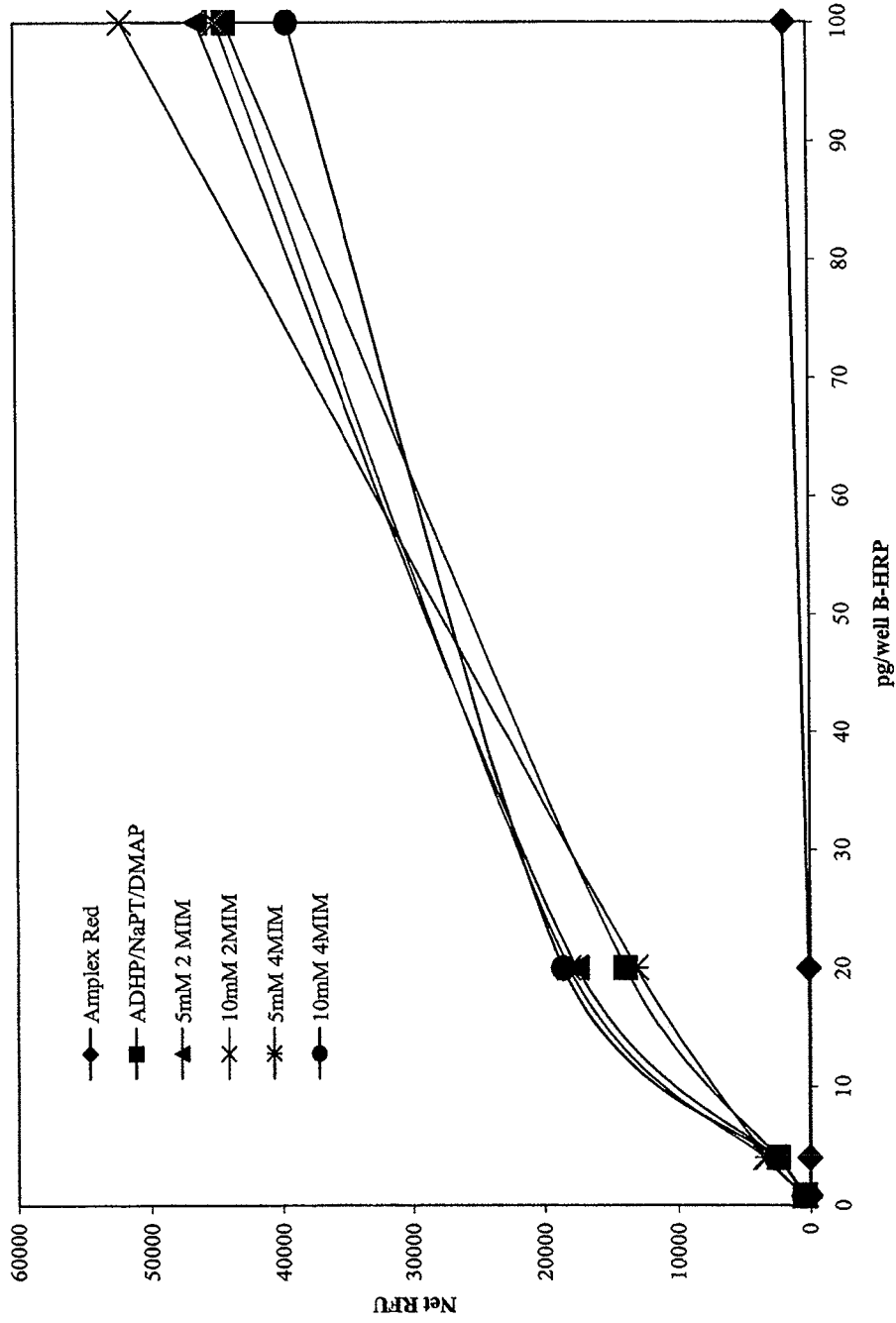
FIG. 2 shows the effect of other embodiments of the ADHP substrate in a peroxidase assay.

The composition comprising NaPT and DMAP or NaPT and IM enhanced the fluorescent product (resorufin) generated by the ADHP reaction with HRP, in the presence of a peroxide source, as shown in FIG. 2.

The Amplex Red® substrate solution was prepared according to manufacturers instructions. The NaPT/DMAP enhanced ADHP substrate was prepared by dissolving 6 mM NaPT and 5 mM DMAP in the Amplex Red® substrate solution. The NaPT/IM enhanced substrates were prepared by adding 6 mM NaPT to the Amplex Red® substrate solution in combination with one of the following: 5 mM 2-methyl imidazole (2MIM), 10 mM 2MIM, 5 mM 4-methyl imidazole (4MIM) or 10 mM 4MIM. The substrates were added to the wells of a black 96 well microplate. A standard curve of biotinylated horseradish peroxidase (B-HRP) was prepared in tris buffered saline (TBS) so that the final concentrations added to the wells of the plate were 100 pg, 20 pg, 4 pg, and 0.8 pg. The B-HRP dilutions and a TBS blank were added to the wells of the plate and incubated for one minute. The fluorescence production was measured using a Tecan Safire Fluorometer with excitation at 560 nm and emission at 590 nm.

As shown in FIG. 2, the results show an increase in signal intensity using enhanced ADHP containing either NaPT/DMAP or NaPT/1M, depending on the HRP concentration.

EXAMPLE 3

The NaPT/DMAP enhancer system was tested for its ability to improve the fluorescent signal production of both Amplex Red® substrate and Amplex UltraRed® substrate in a microplate assay with B-HRP.

The Amplex Red® reagent and Amplex UltraRed® reagent substrate solutions were prepared according to manufacturers instructions. The enhanced versions of both substrates were prepared by dissolving 6 mM NaPT and 5 mM DMAP in the Amplex Red® reagent and Amplex UltraRed® reagent substrate solutions. The substrate solutions were added to the wells of a black 96 well microplate. A standard curve of B-HRP was prepared in TBS so that the final concentrations added to the wells of the plate were 20 pg, 4 pg, 0.8 pg, 0.16 pg, and 0.032 pg. The B-HRP dilutions and a TBS blank were added to the wells of the plate and incubated for 15 minutes. The fluorescence production was measured using a Tecan Safire Fluorometer with excitation at 560 nm and emission at 590 nm.

Figure 3:
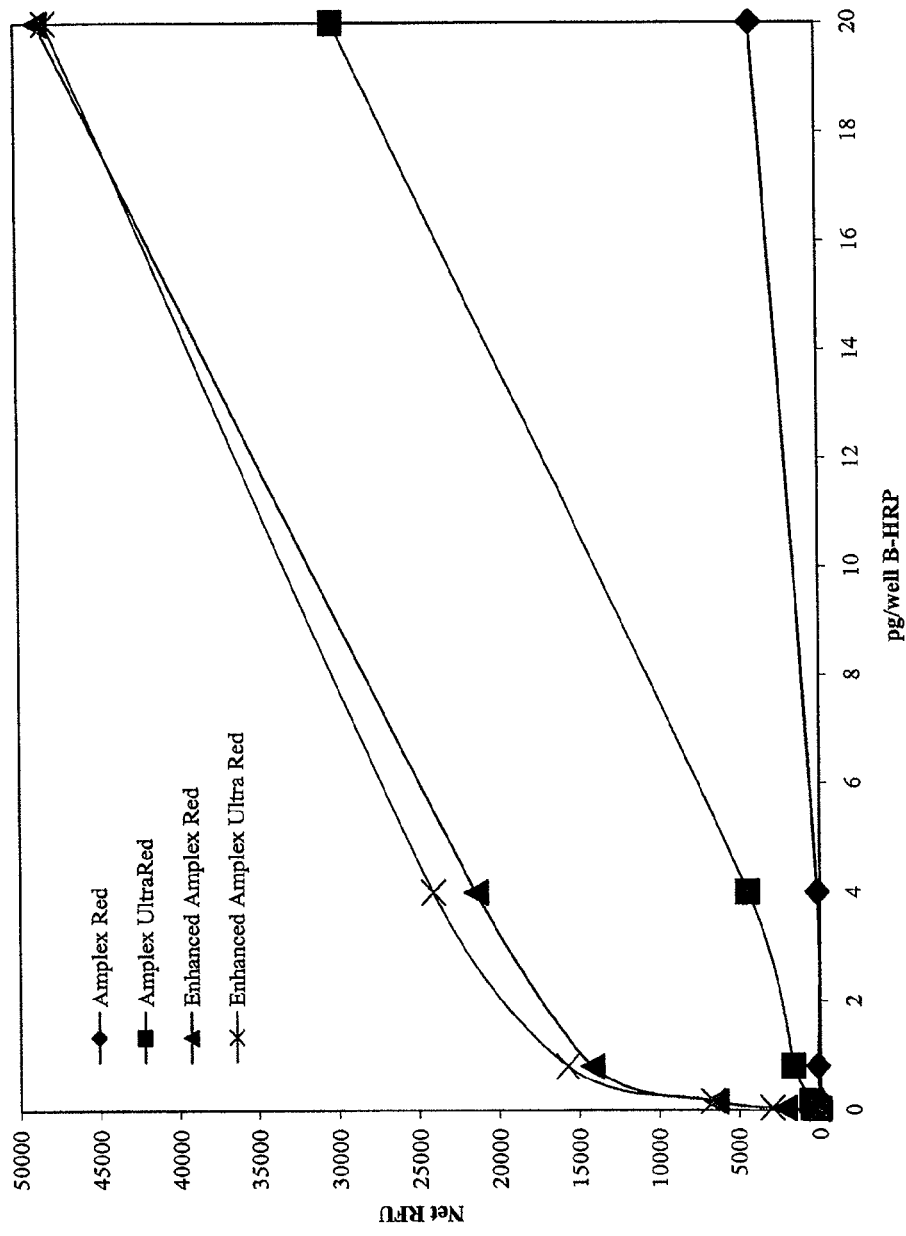
FIG. 3 shows the effect of various embodiments of the ADHP substrate versus other commercially available substrates in a peroxidase assay.

As shown in FIG. 3, the enhancer composition caused an increase in signal production when added to both Amplex Red® reagent and Amplex UltraRed® reagent, with the improvement as much as 20-fold depending on the HRP concentration.

EXAMPLE 4

Assays are conducted as in Examples 1-3 except the chemical enhancer is carboxypropylphenothiazine (CPPT).

EXAMPLE 5

Assays are conducted as in Examples 1-3 except the chemical enhancer is N-(4-sulfo phenyl) phenothiazine.

The composition may be used in a number of assay configurations.

EXAMPLE 6

Plate based assay with biotinylated HRP (B-HRP) in solution (screening assay)

A standard curve of B-HRP is prepared in a dilution buffer such as TBS or PBS. The substrate solution, for example, a resorufin derivative, is prepared and added to the wells of an opaque 96-well microplate, along with a chemical enhancer and a nucleophilic or organic base catalyst and/or an imidazole.

B-HRP dilutions are added to the wells of the plate in duplicate or triplicate for each substrate formulation so that the final B-HRP concentrations in the wells are in the low picogram range. A typical standard curve may be; 100 pg, 20 pg, 4 pg, 0.8 pg, 0.16 pg, 0.032 pg, and 0.0064 pg of B-HRP. The diluent buffer is added to duplicate or triplicate wells as a blank.

The plate containing the chemifluorescent substrate(s) is then read on a plate based fluorometer with the proper excitation and emission wavelengths, for example, 560 nm and 590 nm, respectively. The plate(s) is typically read repeatedly over time, for example, every 30 seconds or every one minute, to determine the kinetic characteristics of the substrate/HRP/peroxide reaction.

The fluorescent intensity, sensitivity and linearity overtime are compared.

EXAMPLE 7

Plate based assay with biotinylated HRP (B-HRP) bound to streptavidin (SA).

A standard curve of B-HRP is prepared in a dilution buffer such as TBS or PBS.

B-HRP dilutions are added to the wells of an opaque streptavidin coated microplate in duplicate or triplicate so that the final B-HRP concentrations are in the low picogram range. A typical standard curve may be; 100 pg, 20 pg, 4 pg, 0.8 pg, 0.16 pg, 0.032 pg, and 0.0064 pg of B-HRP. The diluent buffer is added to duplicate or triplicate wells as a blank.

The plate is incubated for 30 minutes and then washed with wash buffer.

Substrate solutions, for example, a resorufin derivative, are prepared and added to the wells of the washed microplate, along with a chemical enhancer and a nucleophilic or organic base catalyst and/or an imidazole.

The plate containing the chemifluorescent substrate(s) is then read on a plate based fluorometer with the proper excitation and emission wavelengths, for example, 560 nm and 590 nm, respectively. The plate(s) is typically read repeatedly over time, for example, every 30 seconds or every one minute, to determine the kinetic characteristics of the substrate/HRP/peroxide reaction.

The fluorescent intensity, sensitivity and linearity overtime are compared.

EXAMPLE 8

Sandwich ELISA assay

An opaque 96-well microplate is coated with an antibody (capture antibody) specific for an antigen of interest and then the plate is blocked with a protein blocking buffer.

A standard curve of a recombinant protein (antigen) is prepared in an appropriate dilution buffer and added to the wells of the capture plate and incubated one hour at room temperature or overnight at 2° C.-8° C.

The plate is washed with a wash buffer (TBS/0.05% Tween 20).

A biotinylated antibody (detection antibody) is then added to the wells of the plate and incubated for 1 hour at room temperature or overnight at 2° C.-8° C. The plate is washed again. A dilution of HRP conjugated streptavidin is prepared and added to all the wells of the plate and incubated for 30 minutes at room temperature. The plate is washed again.

The substrate solution(s), for example, resorufin derivative, are prepared and added to the wells, along with a chemical enhancer and a nucleophilic or organic base catalyst and/or an imidazole.

The plate containing the chemifluorescent substrate(s) is then read on a plate based fluorometer with the proper excitation and emission wavelengths, for example, 560 nm and 590 nm, respectively.

The plate(s) is typically read repeatedly over time, for example, every 30 seconds or every one minute, to determine the kinetic characteristics of the substrate/HRP/peroxide reaction.

The fluorescence intensity, sensitivity and linearity overtime are compared.

EXAMPLE 9

Figure 4:
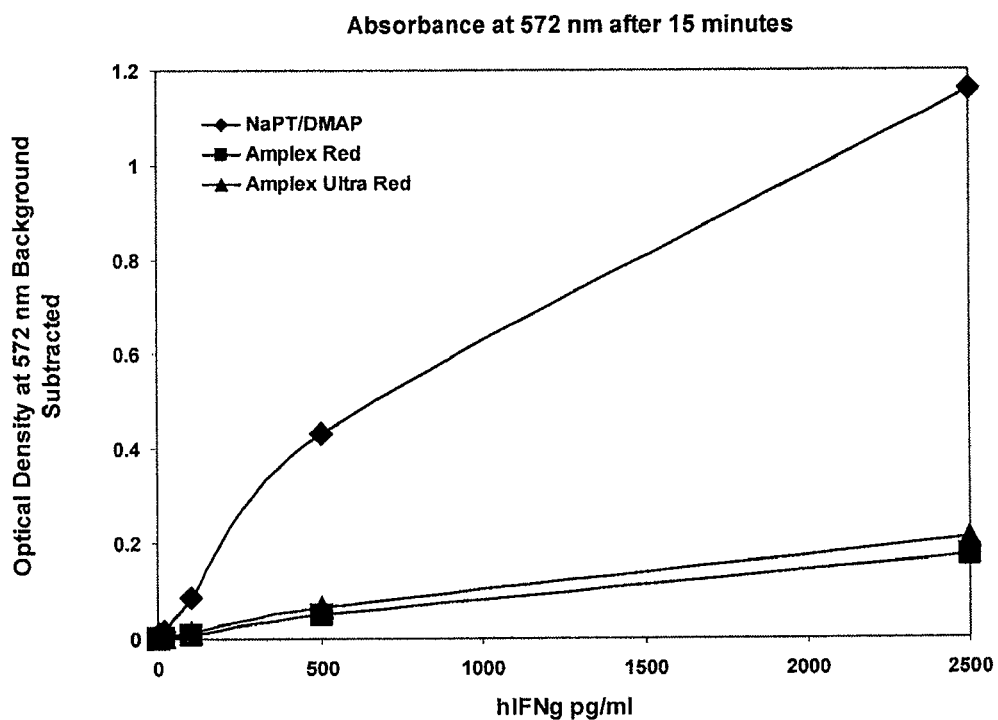
FIG. 4 shows one embodiment of the ADHP substrate in a sandwich ELISA assay.
Figure 4:
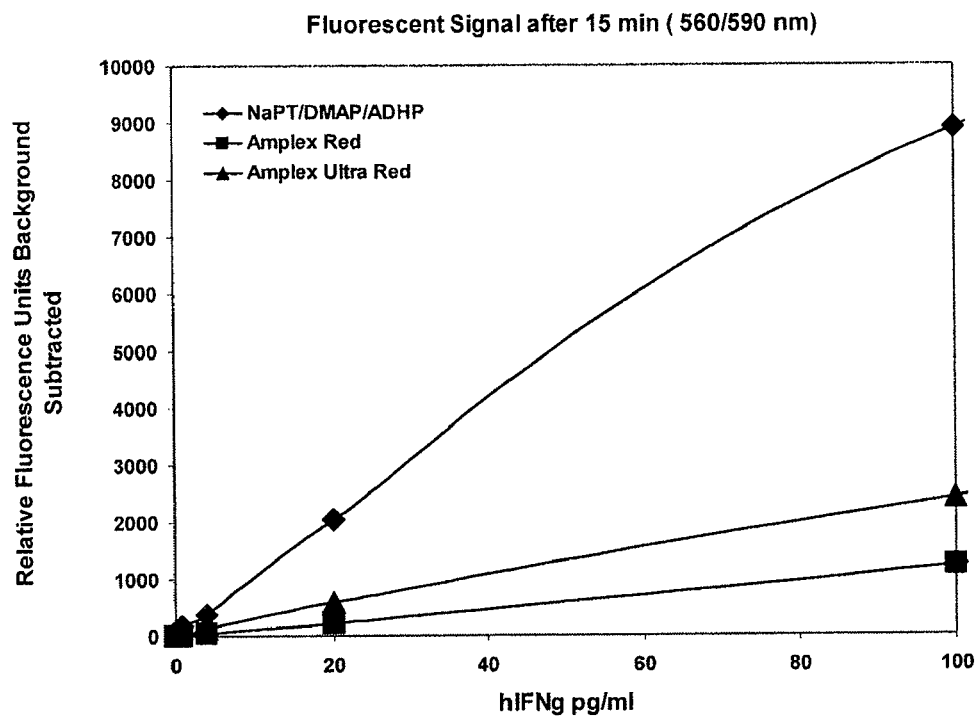

The NaPT/DMAP enhancer system was compared to Amplex® Red reagent and Amplex® UltraRed reagent in a Sandwich ELISA using the procedure outlined in Thermo Scientific, Human Interferon gamma (hIFNγ) ELISA Kit (Product #EHIFNG) instructions. A standard curve of recombinant hIFNγ was used as the samples. Both the colorimetric and fluorescent signals were measured. Amplex® Red reagent and Amplex® UltraRed reagent substrate working solutions were prepared according to the manufacturers instructions. NaPT (3 mM) and 5 mM DMAP were dissolved in TBS buffer pH 7.4 with 100 µM ADHP and 4 mM perborate. The substrate solutions were added to the wells of the plate and after a 15 minute incubation the colorimetric signal was read using a Tecan Safire multimode reader with absorbance at 572 nm (FIG. 4). The same plate was read for fluorescence signal at 560/590 nm (FIG. 4). As shown in FIG. 4, ADHP with NaPT/DMAP enhancer system outperformed Amplex® Red substrate and Amplex® Ultra Red HRP substrate. The detection range of recombinant hIFNγ using colorimetric detection of absorbance at 572 nm was 4-2500 pg/ml for the NaPT/DMAP enhanced substrate. Amplex®Red substrate and Amplex UltraRed substrate were able to detect a range from 100-2500 pg/ml and 20-2500 pg/ml, respectively, of recombinant hIFNγ. The fluorescent signal was also more intense with the NaPT/DMAP enhanced ADHP system when compared to both Amplex® Red substrate and Amplex® UltraRed substrate. The fluorescent detection range for NaPT/DMAP enhanced ADHP was 0.16-2500 pg/ml of recombinant hIFNγ. Amplex® Red substrate and Amplex® UltraRed substrate both detected in the range of 4-2500 pg/ml of recombinant hIFNγ.

EXAMPLE 10

CPPT and NaPX were tested in combination with DMAP to determine their effectiveness as enhancers of resorufin production from the reaction of ADHP with HRP. A standard curve of B-HRP was prepared in TBS buffer so that the final concentrations added to the wells of the plate were 1000 pg, 333.3 pg, 111.1 pg, 37.0 pg, 12.3 pg, 4.1 pg, and 1.4 pg. The B-HRP dilutions and a TBS buffer blank were added to the wells of a black 96 well neutravidin coated microplate. The plate was incubated for 1 hour to allow the B-HRP time to bind to the neutravidin and then washed with TBS buffer. The enhanced ADHP substrates were prepared by dissolving 3 mM CPPT and 5 mM DMAP or 3 mM NaPX and 5 mM DMAP in TBS Buffer with 100 µM ADHP and 4 mM perborate. The substrates were added to the wells of the plate and incubated for 10 minutes. The fluorescence production was measured using a Tecan Safire Fluorometer with excitation at 560 nm and emission at 590 nm.

Figure 5:
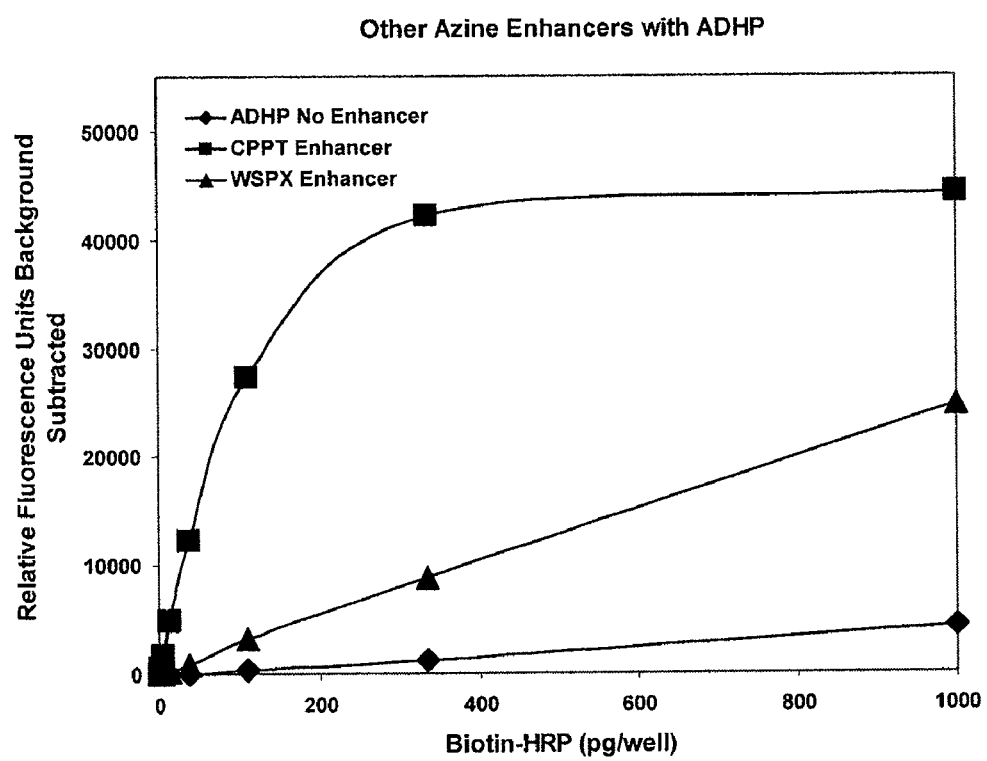
FIG. 5 shows the fluorescence enhancement effects of other azine enhancers combined with the ADHP substrate.

As shown in FIG. 5, both the enhancer compositions caused an increase in signal production when added to a substrates solution containing ADHP.

Other variations or embodiments will also be apparent to one of ordinary skill in the art from the above figures, description, and examples. Thus, the foregoing embodiments are not to be construed as limiting the scope of the following claims.

What is claimed:

1. A kit for detecting analytes that produce peroxide or exhibit peroxidase activity, the kit comprising
    a resorufin derivative 10-acetyl-3,7-dihydroxyphenoxazine (ADHP),
    a chemical enhancer sodium phenothiazine 10-yl propane sulfonate (NaPT),
    an organic base catalyst dimethylaminopyridine (DMAP) and/or a 2-methyl imidazole,
    a peroxide source, and
    a buffer solution,
    wherein the kit provides reagents for the detection of analytes that produce peroxide or peroxide activity.

2. The kit of claim 1 further comprising at least one of horseradish peroxidase (HRP), HRP conjugated streptavidin, or HRP conjugated antibodies.

3. The kit of claim 1 wherein the peroxide source is selected from the group consisting of hydrogen peroxide, urea peroxide, perborate and combinations thereof.

4. The kit of claim 1 wherein the buffer is selected from the group consisting of tris buffer saline, phosphate buffered saline, and combinations thereof.

* * * * *